United States Patent
Zaias et al.

[11] Patent Number: 5,131,417
[45] Date of Patent: Jul. 21, 1992

[54] METHOD OF RATING HAIR DAMAGE

[76] Inventors: Nardo Zaias, 36 Star Island, Miami Beach, Fla. 33139; Syed Pervaiz, 4320 NW. 79th Ave., Apt. 1E, Miami, Fla. 33166

[21] Appl. No.: 791,674

[22] Filed: Nov. 14, 1991

[51] Int. Cl.$^5$ ............................................... A45D 7/04
[52] U.S. Cl. .................................. 132/204; 132/200; 132/203; 424/70; 424/71
[58] Field of Search ............... 132/200, 202, 203, 204, 132/205, 206, 207, 208, 209, 210, 211; 424/70, 71

[56] References Cited

U.S. PATENT DOCUMENTS 3,472,243 10/1969 Wall et al. ............................ 132/202
3,472,604 10/1969 Dasher et al. ........................ 132/202
4,970,067 11/1990 Panandiker et al. ................. 132/203
4,971,080 11/1990 Rubinstein ........................... 132/202

*Primary Examiner*—Gene Mancene
*Assistant Examiner*—Frank A. LaViola
*Attorney, Agent, or Firm*—Shlesinger, Arkwright & Garvey

[57] ABSTRACT

A method of obtaining a hair damage rating is obtained by determining the change in hair structure, such as measuring the amount of free sulfhydryl groups after hair treatment or exposure to agents, comparing this with a number of such groups before treatment to obtain a percentage change, establishing a rating scale having a range of percentage change values, and selecting the hair damage factor a number corresponding to the determined percentage change after treatment.

8 Claims, No Drawings

METHOD OF RATING HAIR DAMAGE

BACKGROUND OF THE INVENTION

There are many different types of hair products on the market, all of which have an effect on hair, the products containing many different types of chemicals designed for specific purposes, such as shampoos, rinses, permanent waves, and hair set. These products, although accomplishing the purposes for which they are designed, also have an adverse effect on the hair itself. There has not been any concern, until recently, as to the extent of damage caused.

Consequently, there is a need for an evaluation of hair damage caused by such products, to both advise the public, and to also give the manufacturer an indication of the amount of damage caused by his product, by accurately gauging various formulations in order to select the one having the least adverse effect to hair.

SUMMARY OF THE INVENTION

Accordingly, the subject of the invention is directed to a method of rating hair damage, and particularly to a system that would rank those products marketed for hair use, providing both the manufacturer and the consumer with an indication of the adverse side effects of the product.

The determination of hair damage evaluates hair protein damage in the hair in the context of a rating scale for the full range of hair damage from minimum to maximum adverse affect.

The rating technique of the present invention provides an accurate assessment of hair damage in the form of a rating number. The adoption of a rating number standard will give an understanding of how much hair products, such as cosmetic hair products, for example, will damage the hair. When used with consumer products, the consumer will have an understanding of the amount of adverse effect of a particular product. Consequently, with the potential damage to hair being a factor in consumer selection, an incentive is provided to manufacturers to market products that have the lowest hair damage rating attainable.

Accurate reading to a degree not possible previously, is now possible and provides the ability to make an accurate, reliable and practical rating system possible.

DESCRIPTION OF THE INVENTION

In the past measurements of hair damage, was based on loss of mechanical tensile strength. However a chemical change in molecular hair structure, where disulfide bonds, namely disulfide bonds are broken, producing free sulfhydryl groups is also measurable and appears to be more accurate than tensile strength tests.

Measurement of the disruption of disulfide bonds, using the tension techniques to measure the number of free sulfhydryl groups in hair, using substances that will react with such free groups, and which can be detected.

For example, samples of hair exposed to hair preparations which have agents that cause damage to hair, can be treated with a solution, such as iodoacetic acid to obtain an accurate reading of the number of free sulfhydryl groups, the more there are, the greater the damage.

In order to make the system meaningful, the percent of measured broken bonds, and not the magnitude change of broken bonds must be determined. Once this percentage change for a given hair sample is determined, it is compared to a scale of percent increase of hair damage, as indicated as a percentage of free sulfhydryl groups, set forth in incremental value steps, to determine the hair damage factor number (HDF). This number will give a direct correlation of hair damage sustained as a result of hair treatment, whether by use of a permanent wave, shampoo, etc. Consequently, the typical hair damage factor number (HDF) provides a consumer with information concerning the amount of hair damage to be sustained by a given treatment or product.

A scale of values, noted as the hair destruction factor (HDF) has been constructed on the basis of the number of free sulfhydryl groups, for a hair damaged, representing a low damage scale, HDF (weak) is as follows:

| HDF(W) | Percent Increase in Free Sulfhydryl Groups |
|---|---|
| 99.9 | 99.9% |
| 90 | 90% |
| 80 | 80% |
| 70 | 70% |
| 60 | 60% |
| 50 | 50% |
| 40 | 40% |
| 30 | 30% |
| 20 | 20% |
| 10 | 10% |
| 5 | .1% |
| 1 | 1% |
| 0 | 0% |

For example, an HDF rating of 60(W) would be given to a product where there was a 60% increase in free sulfhydryl groups imparted to hair when that product was used, according to before and after tests.

These free SH tests are based upon the general make up of a hair fiber, which is a structural arrangement of proteins, namely, alpha-helical, low sulfur keratins in the cortex, which are embedded in matrix high sulfur keratins. These proteins are linked together by extensive cross-linking by disulfide bonds (both inter- and intra-chain course linking, involving cysteines), which impart the mechanical strength to the hair itself. A decrease in cysteine content will produce low levels of cross-linking causing brittleness of the hair shaft.

A radioactive bonding and detection technique of testing can be used to obtain information with respect to the amount of disruption of disulfide bonds that have been broken.

EXAMPLE 1:

A sample of treated hair in the amount of 1-2 mg is cut into 1-2 mm pieces and mixed with 8M urea or 6M guanidine hydrochloride and 0.4M Tris, pH9.5. The pH is then brought to 8.5, and then Iodoacetic acid is added and the mixture incubated, in the dark, at room temperature. After twenty (20) minutes, cold Iodoacetic acid is added to bring the mix to a final concentration of 10 mM, and the mixture is incubated again for another twenty minutes in the same manner.

At the end of incubation, dithiothreotol (Cleland's reagent) is added to a final concentration of 20 mM. This mixture is incubated at 37° Centigrade for 2 to 4 hours to achieve complete reduction of disulfide bonds.

After the conclusion of this treatment, cold Iodoacetic acid is added to the mixture at a final concentration of 50 mM and incubated at room temperature for twenty minutes. The proteins in the mixture are then precipitated by adding 5% ice-cold trichloroacetic acid (TCA). Then, free iodoacetic acid (cold and radioactive), and other reaction products, are removed by washing the precipitated proteins with 20 ml of 5% ice-cold ICA using a 45 Mu Millipore glass fiber filter. After drying, the filter is dissolved in scintillation mixture and counted for radioactive carbon 14 or hydrogen 3.

There is a second scale for more extensive damage, which starts with a 100% damage or alteration above the HDF(W) scale discussed above, which is as follows:

| HDF(S) | Percent Increase (Free Sulfhydryl Groups) |
| --- | --- |
| 99.9(S) | 999.4 |
| 90(S) | 900 |
| 80(S) | 800 |
| 70(S) | 700 |
| 60(S) | 600 |
| 50(S) | 500 |
| 40(S) | 400 |
| 30(S) | 300 |
| 20(S) | 200 |
| 10(S) | 100 |
| 0(S) | 99.9–100 |

The HD factor scale permits the direct reading of the amount of broken disulfide bonds from the tests to be converted to a rating which is readily useable for comparison purposes, as a standard. This rating capability has not be possible heretofore.

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention your limits of the claims appended hereto.

We claim:

1. The method of providing a rating of hair damage, comprising the steps of:
    a) exposing a hair sample to an agent which will cause hair damage by breaking disulfide bonds;
    b) obtaining a reading on the number of broken disulfide bonds;
    c) converting the number of broken bonds to a percentage increase relative to a pretreatment number of such bonds; and,
    d) comparing the percentage increase with a preestablished hair damaged factor scale covering a full range of percentage increase potential readings to find a rating number which indicates the amount of hair damage incurred.

2. The method of obtaining a hair damage rating as set forth in claim 1, including the step of:
    a) obtaining the damage control factor rating scale by correlating a range of hair destruction factor numbers (HDF) with a full preselected range of percent alteration of broken disulfide bonds in a hair sample.

3. The method of obtaining a hair damage rating as set forth in claim 1, including the step of:
    a) obtaining the number of broken disulfide bonds in the hair sample by a radioactive measuring technique.

4. The method of obtaining a hair damage rating as set forth in claim 2, including the providing of:
    a) a scale for a low damage reading produced by the altering agent on the hair for low extent of hair damage;
    b) a second scale for high damage beyond a 100% damage or alteration of the hair sample.

5. The method of obtaining a hair damage rating as set forth in claim 3, including the step of:
    a) using radioactive iodoacetic acid as the reactant in a solution having a pH in the range of 7.5 to 9.

6. The method of obtaining a hair damage rating as set forth in claim 4, including the step of:
    a) providing successive incremental steps in the scale which are uniform percentage increases in free sulfhydryl groups.

7. The method of obtaining a hair damage rating as set forth in claim 6, including the steps of:
    a) obtaining the number of broken disulfide bonds in the hair sample by a broken bond sulfhydryl measuring technique; and,
    b) providing incremental steps in the scale which are uniform percentage increases in free sulfhydryl groups.

8. The method of obtaining a hair damage rating as set forth in claim 7, including the steps of:
    a) obtaining the number of broken disulfide bonds in the hair sample by a radioactive measuring technique; and
    b) using radioactive iodoacetic acid as the reactant in a solution having a pH in the range of 7.5 to 9.

* * * * *